United States Patent
Mejia et al.

(10) Patent No.: US 9,901,438 B2
(45) Date of Patent: Feb. 27, 2018

(54) METHOD OF MANUFACTURING BREAST IMPLANTS WITH INTEGRATED TRANSPONDERS

(71) Applicant: JAMM TECHNOLOGIES, INC., La Garita (CR)

(72) Inventors: Ezequiel Mejia, Woodbury, MN (US); Randolph Keith Geissler, Hudson, WI (US); Juan Jose Chacon Quiros, Alajuela (CR)

(73) Assignee: Jamm Technologies, Inc., Alajuela (CR)

( * ) Notice: Subject to any disclaimer, the term of this patent is extended or adjusted under 35 U.S.C. 154(b) by 366 days.

(21) Appl. No.: 14/028,193

(22) Filed: Sep. 16, 2013

(65) Prior Publication Data

US 2014/0081398 A1   Mar. 20, 2014

Related U.S. Application Data

(60) Provisional application No. 61/701,910, filed on Sep. 17, 2012.

(51) Int. Cl.
*B29C 41/02*  (2006.01)
*A61F 2/12*  (2006.01)
*B29C 41/14*  (2006.01)

(52) U.S. Cl.
CPC .......... *A61F 2/12* (2013.01); *B29C 41/02* (2013.01); *B29C 41/14* (2013.01); *A61F 2250/0096* (2013.01)

(58) Field of Classification Search
None
See application file for complete search history.

(56) References Cited

U.S. PATENT DOCUMENTS

| | | | |
|---|---|---|---|
| 4,863,470 A | 9/1989 | Carter | |
| 5,300,120 A | 4/1994 | Knapp et al. | |
| 5,545,220 A | 8/1996 | Andrews et al. | |
| 5,653,758 A | 8/1997 | Daniels et al. | |
| 5,674,288 A | 10/1997 | Knapp et al. | |
| 5,716,407 A | 2/1998 | Knapp et al. | |
| 5,725,578 A * | 3/1998 | Knapp ............... | A01K 11/006 128/898 |
| 5,824,081 A | 10/1998 | Knapp et al. | |
| 5,833,603 A | 11/1998 | Kovacs et al. | |
| 5,855,609 A | 1/1999 | Knapp | |

(Continued)

FOREIGN PATENT DOCUMENTS

| WO | WO 96/22058 A1 | 7/1996 |
|---|---|---|
| WO | WO 2008/014283 A2 | 1/2008 |
| WO | WO 2010/056610 A2 | 5/2010 |

OTHER PUBLICATIONS

International Search Report and Written Opinion dated Dec. 5, 2013 in International Application No. PCT/US2013/059988.

(Continued)

*Primary Examiner* — Edmund Lee
(74) *Attorney, Agent, or Firm* — Bookoff McAndrews, PLLC

(57) ABSTRACT

The present invention provides, in various embodiments, a breast implant with an RFID transponder embedded therein, so that the implant can be conveniently identified while inside the human body, and methods of making the same.

16 Claims, 2 Drawing Sheets

(56) References Cited

U.S. PATENT DOCUMENTS

| | | | |
|---|---|---|---|
| 5,977,431 A * | 11/1999 | Knapp | A61B 5/117 623/23.72 |
| 2009/0149953 A1 | 6/2009 | Schuessler et al. | |
| 2009/0270985 A1* | 10/2009 | Schuessler | A61F 2/12 623/8 |
| 2010/0049316 A1* | 2/2010 | Schuessler | A61B 19/24 623/8 |
| 2010/0094416 A1 | 4/2010 | Maguire et al. | |
| 2010/0228347 A1* | 9/2010 | Schuessler | A61F 2/12 623/8 |
| 2011/0029076 A1 | 2/2011 | Paletta et al. | |
| 2011/0046729 A1 | 2/2011 | Schuessler et al. | |
| 2011/0137413 A1 | 6/2011 | Osypka | |
| 2011/0257743 A1* | 10/2011 | Schuessler | A61F 2/12 623/8 |
| 2012/0165934 A1 | 6/2012 | Schuessler | |
| 2013/0013063 A1 | 1/2013 | Del Vecchio | |
| 2013/0131800 A1 | 5/2013 | Schuessler | |

OTHER PUBLICATIONS

European Search Report for corresponding Application No. 13839796.3 dated Mar. 29, 2016 (2 pages).

\* cited by examiner

1a, MICROCHIP INSERTION

1b, MICROCHIP INSERTION

INSERTION OF MICROCHIP INTO A BREAST IMPLANT

2a, POSITION OF MICROCHIP

2b, POSITION OF MICROCHIP

AREA OF LOCATION OF MICROCHIP

3a, CURING OVEN

3b, CURING OVEN

CURING CYCLE FOR LOCATION OF THE MICROCHIP IN THE BREAST IMPLANT

4a, VACCUM CHAMBER

4b, VACCUM CHAMBER

VACCUM CYCLE FOR LOCATION OF THE MICROCHIP IN THE BREAST IMPLANT

METHOD OF MANUFACTURING BREAST IMPLANTS WITH INTEGRATED TRANSPONDERS

RELATED APPLICATIONS

This application claims the benefit of, and priority to, U.S. Provisional Application No. 61/701,910, filed Sep. 17, 2012, entitled "Breast Implants With Integrated Transponders," which is incorporated herein by reference in its entirety.

BACKGROUND

Currently there is no accurate, adequate, practical or economical way to identify a breast implant that is already inside the body of a patient. This void has developed into a serious complication for the fulfillment of recalls and controls, when the patients do not have the identification information for their implants, or when medical records are not available. More specifically, and relating to defective breast implants which have been already found in the market, many women around the world face the problem of having no information regarding the breast implants inside them, and no way of finding out if they need to be explanted or not, without undergoing an actual explantation procedure. Thus, there is a need in the art for breast implants that, when implanted, can be easily and accurately identified from outside the body.

SUMMARY

The present invention relates to a breast implant designed to add to or replace volume of the breast, which includes a unique device identifier (UDI) therein, providing post-implantation device recognition and traceability. In preferred embodiments, the UDI is a passive RFID (radio frequency identification) transponder, which is embedded within the implant filling at the time of manufacture.

In various embodiments, the present invention provides breast implant comprising a silicone elastomer shell with an opening covered by a patch, a silicone gel filling said shell, and a transponder disposed within said filling and positioned proximal to said patch.

The silicone elastomer shell is formed by preparing a silicone elastomer dispersion; dipping a mold into said dispersion one or more times, forming one or more silicone elastomer layers; and removing the one or more layers from the mold, forming a silicone elastomer shell having an opening where the mold was removed.

In some embodiments, the transponder is placed within the shell through said opening. Said opening is then covered with a patch and the patched shell is filled with a silicone gel through a filling hole in the patch.

In other embodiments, said opening is covered with a patch, the patched shell is filled with a silicone gel through a filling hole in the patch, and the transponder is placed within the patched shell through said filling hole.

In still further embodiments, said opening is covered with a patch, the transponder is placed within the patched shell through a filling hole in the patch, and the patched shell is filled with a silicone gel through said filling hole.

The manufacturing process further includes applying a vacuum to the silicone gel-filled shell, removing air bubbles and positioning the transponder proximal to said patch; sealing the filling hole; and curing the silicone gel, wherein said gel curing further positions the transponder proximal to said patch and comprises heating the silicone-gel filled shell with transponder therein to a temperature of about 140° C. to 200° C. for up to about 8 hours.

In some embodiments, the breast implant with integrated transponder is further sterilized at a temperature of about 120° C. to 150° C. for up to about 36 hours.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of the preferred embodiments of the application, will be better understood when read in conjunction with the appended drawings. For the purposes of illustrating the device of the present application, there are shown in the drawings preferred embodiments. It should be understood, however, that the application is not limited to the precise arrangements and instrumentalities shown. In the drawings.

DETAILED DESCRIPTION

The present invention provides, in various embodiments, a breast implant with an RFID transponder embedded therein, so that the implant can be conveniently identified while inside the human body, and methods of making the same. The transponder contains a unique identification code and/or implant-specific information that is readily accessible, for example, by an external handheld scanner. In some embodiments, identification information from the transponder can be used to access one or more databases containing further information (regarding the specific breast implant, the specific patient, etc.).

Figure 1:
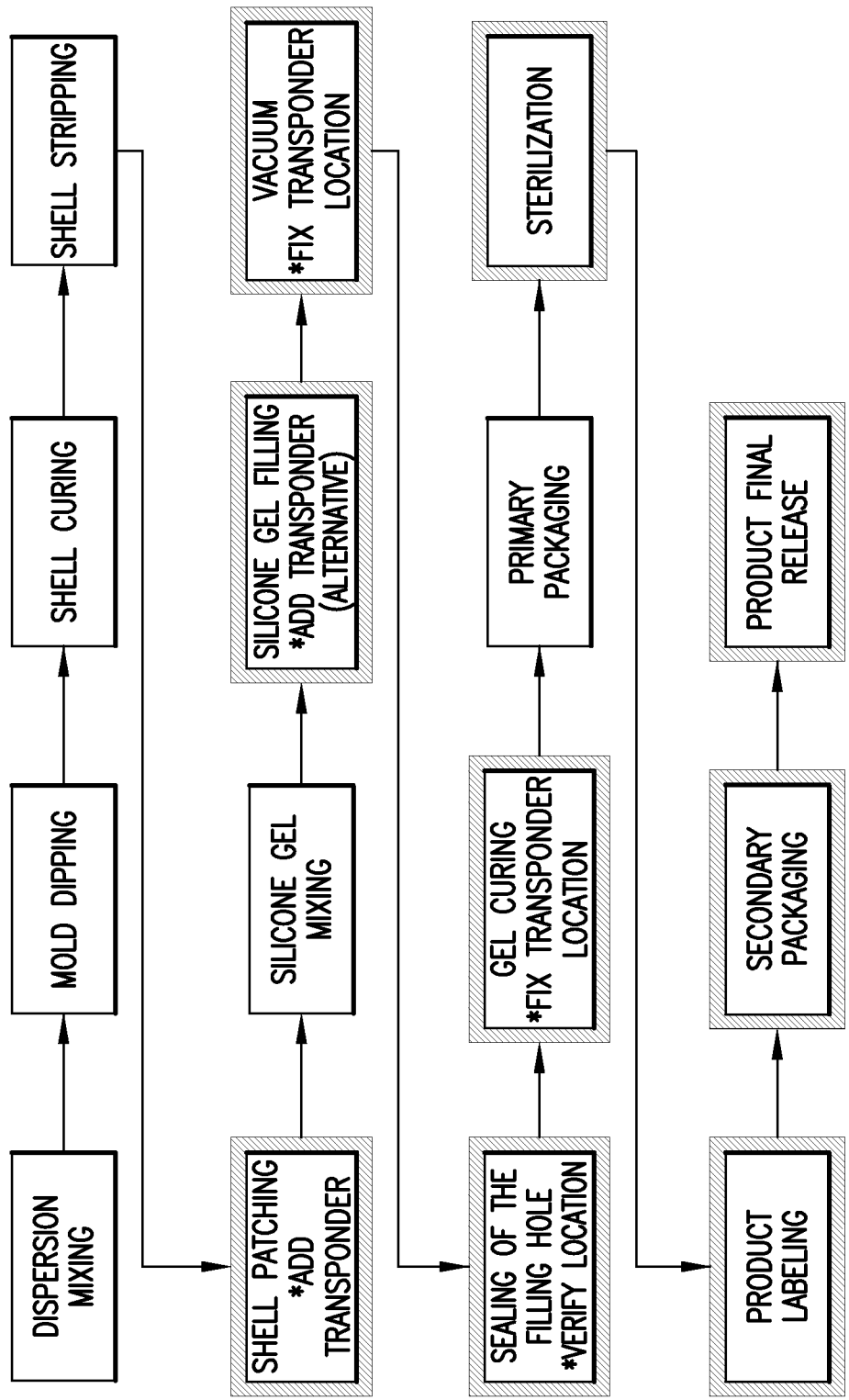
FIG. 1 shows a flowchart of exemplary processes involved in manufacturing the breast implants of the present invention, according to some embodiments.

FIG. 1 shows an exemplary flowchart of the different processes involved in the manufacturing of a breast implant of the present invention, according to some embodiments. The processes affected by inclusion of a transponder are highlighted, and points where the transponder is added/fixed/verified are marked with an asterisk.

In some embodiments, the breast implant comprises a silicone elastomer shell. As shown in FIG. 1, this shell may be formed by preparing/mixing a silicone elastomer dispersion, and dipping a mold or mandrel into the dispersion. Multiple dip coats may be used to obtain a multilayered shell, and different dispersions may be used for different dip coats. For example, a colored barrier layer may be added to the shell, as described in U.S. application Ser. No. 13/412,221. The shell is then cured and removed/stripped from the mold.

The aperture (open part of the shell where the mold was removed) is then patched, for example, with a piece of silicone elastomer similar to the cured shell. In some embodiments, the transponder is introduced into the breast implant during the shell patching (through the opening in the shell before the shell is patched). The patch is preferably secured by high pressure and heat. Alternatively, an adhesive or other method may be used to secure the patch. The patched silicone elastomer shell may be dried and cured, and is then filled (e.g., by a syringe) through a hole in the patch system (including the area where the patch joins with the shell) to a predetermined weight with fluid or gel. In some embodiments, the transponder is added during the silicone gel filling, through the hole used for the silicone gel filling. As shown in FIG. 1, in some embodiments, a highly viscous and highly elastic silicone gel is mixed and used (uncured) for filling the breast implant. The silicone gel may include a platinum catalyst. The filled implant is then placed in a vacuum chamber, where it undergoes one or more cycles of vacuum. If there are any bubbles still visible, additional vacuum cycles may be added.

The hole through which the implant was filled is then sealed (e.g., with an RTV silicone adhesive), and the silicone gel is cured. Preferably, the gel curing comprises high temperature curing (e.g., about 160° C.). In some embodiments, the implant may be filled with liquid or alternate fillers, which do not need further curing or vacuum cycles. The breast implant may then be cooled down to room temperature and placed in primary packaging (e.g., a double pack comprising a pair of implants). Sterilization may then be performed. Sterilization is preferably performed using dry heat (e.g., about 120 to 130° C. for about 24 to 48 hours). Alternatively, the implant may be sterilized using other sterilization methods, such as ethylene oxide.

Product labeling and secondary packaging processes are then performed before the final release of the product. In some embodiments, for example, product labeling assigns a serial number to the implant, and stores the serial number with information about the associated implant in a computer database (e.g., in an ERP system). Secondary packaging assigns the transponder identification code (e.g., 16 digit code) with the serial number of the implant. Product final release verifies that the transponder identification code matches the serial number of the implant. In other embodiments, different labeling/packaging processes may be used, as long as they match the transponder identification number to the serial number of each device.

Notably, Applicant has determined that the placement of the transponder within the breast implant is important for safe and effective function of the invention. For example, in some embodiments, the transponder may be affixed to the breast implant shell. However, the transponder is fragile and could break and/or could puncture the implant shell, thus it is preferred to place the transponder in a stronger part of the product. Accordingly, in other, more preferred embodiments, the transponder is suspended within the implant filling, close to the patch.

Figure 2:
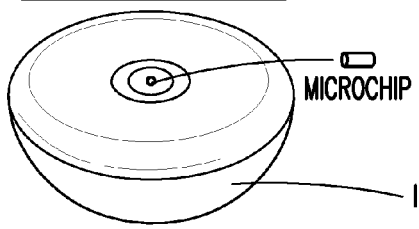
FIG. 2 shows a schematic diagram of breast implants of the present invention, according to some embodiments, illustrating exemplary placement of a microchip/transponder.
Figure 2:
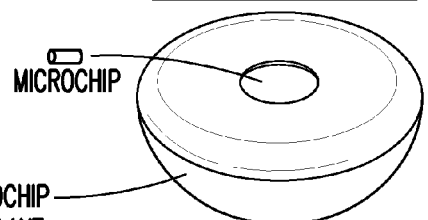
Figure 2:
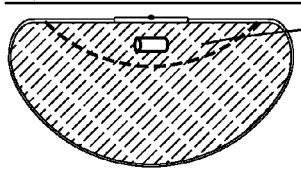
Figure 2:
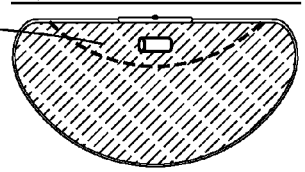
Figure 2:
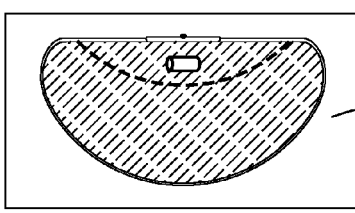
Figure 2:
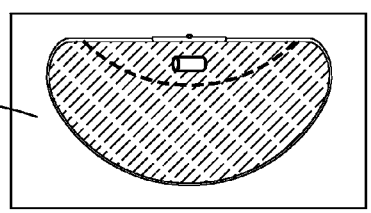
Figure 2:
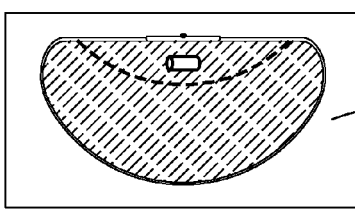
Figure 2:
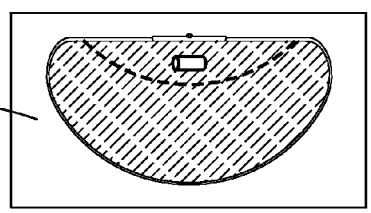

As indicated in FIG. 1, the transponder (microchip) can be added to the implant at different parts of the manufacturing process. For example, as shown in FIG. 2, the transponder can be incorporated during the Shell Patching (through the opening in the shell before patching; 1b). Alternatively, the transponder can be incorporated during the Silicone Gel Filling (through the hole in the patch system used for silicone gel filling; 1a).

In preferred embodiments, the transponder in the silicone gel is free floating, but in close proximity to the patch, which is at the back side of the implant (FIG. 2; 2a, 2b). Accordingly, once implanted, the transponder will be farthest from the exterior of the patient, which can protect the transponder and also ensure that it will not be felt (e.g., under the patient's skin when touched). The density of the silicone gel mixed for the implant filling is thus chosen so that the transponder will float in the silicone gel near the surface (the patch area). The transponder placement in the silicone filling gel at the back of the patch system is adjusted/fixed during the vacuum process (FIG. 2; 4a, 4b), and is verified when the filling hole is sealed.

Preferably, the transponder is added before the silicone gel is cured, so that is secured by the silicone. If the transponder is added after curing, it will break the gel when it is inserted and will not be well-integrated. The transponder placement in the silicone gel near the patch is further adjusted/fixed during the gel curing process (FIG. 2; 3a, 3b). Advantageously, when the gel is cured with the transponder embedded therein, the transponder is flexibly fixed in the gel, and like a rubber band will come back to the same location even when the implant is manipulated/deformed and the transponder is moved therein.

As described above and shown in FIG. 1, several breast implant manufacturing steps involve high temperatures, and high and low pressures. For example, gel curing may use a temperature up to about 200° C. (e.g., between 120° C. and 190° C.) for up to 8 hours. Sterilization may use a temperature up to about 150° C. (e.g., between 110° C. and 145° C.) for up to 48 hours. Transponders integrated within the implants as described herein, must be able to withstand such manufacturing conditions.

Advantageously, the present invention uses a high temperature-stable glass encapsulated transponder, which can withstand temperatures up to 210° C. (±20° C.) and can be integrated into the body of the breast implant during the manufacture of the implant without loss of function thereafter. Such transponders are described in co-pending U.S. application Ser. No. 14/027,896, entitled "High Temperature Transponders," which is incorporated herein by reference in its entirety. In addition to their resistance to heat changes, these transponders provide good shock resistance, long term reliability, long range sensitivity, and small size, among other advantages.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

The invention claimed is:

1. A method of manufacturing a breast implant having a transponder disposed therein, comprising:
    placing a mold into a silicone material one or more times to form a shell comprising one or more silicone layers;
    removing the mold from the shell, wherein the shell has an opening where the mold was removed;
    covering the opening with a patch;
    after covering the opening, placing the transponder radially inward of the shell through a hole in the patch;
    filling the shell with a silicone gel through the hole in the patch such that the transponder is disposed within the silicone gel; and
    curing the silicone gel, wherein the transponder is disposed within the cured silicone gel radially inward of the patch.

2. The method of claim 1, wherein the transponder is flexibly fixed within the cured silicone gel adjacent to the patch.

3. The method of claim 1, further comprising sterilizing the breast implant at a temperature ranging from about 120° C. to about 150° C. for up to about 36 hours.

4. The method of claim 1, further comprising applying a vacuum to the silicone gel-filled shell before curing the silicone gel.

5. The method of claim 1, wherein curing the silicone gel comprises heating the silicone gel with the transponder therein at a temperature ranging from about 140° C. to about 200° C.

6. A method of manufacturing a breast implant, the method comprising:
   preparing a silicone shell defining a cavity, the shell including an aperture;
   covering the aperture with a patch;
   introducing a silicone gel into the cavity;
   introducing a transponder into the cavity, wherein the transponder is movable within the silicone gel relative to the shell, while being in proximity of the patch; and
   curing the silicone gel with the transponder disposed therein to fix a position of the transponder within the silicone gel.

7. The method of claim 6, further comprising removing air from the silicone gel inside the cavity before curing the silicone gel.

8. The method of claim 6, wherein the transponder is flexibly fixed within the cured silicone gel adjacent to the patch.

9. The method of claim 6, wherein the transponder is configured to withstand temperatures up to 210° C. during curing of the silicone gel.

10. The method of claim 6, wherein curing the silicone gel comprises heating the silicone gel with the transponder disposed therein at a temperature ranging from about 140° C. to about 200° C. for up to about 8 hours.

11. The method of claim 6, wherein introducing the silicone gel into the cavity comprises injecting the silicone gel into the cavity through a hole in the patch.

12. The method of claim 6, wherein the transponder is glass encapsulated.

13. A method of manufacturing a breast implant, the method comprising:
    preparing a silicone shell defining a cavity, the shell including a hole;
    placing a transponder into the cavity;
    covering the hole with a patch;
    filling the shell with a silicone gel, wherein the transponder is movable within the silicone gel relative to the shell, while being in proximity of the patch;
    and
    curing the silicone gel to fix a position of the transponder in the silicone gel.

14. The method of claim 13, wherein the silicone gel is cured at a temperature ranging from about 140° C. to about 200° C.

15. The method of claim 13, wherein the transponder is disposed within the cured silicone gel adjacent to the patch.

16. The method of claim 13, wherein the transponder is a high temperature-stable radio-frequency transponder.

\* \* \* \* \*